(12) United States Patent
Terao et al.

(10) Patent No.: US 6,468,713 B1
(45) Date of Patent: Oct. 22, 2002

(54) PHTHALOCYANINE COMPOUNDS, PROCESS FOR PRODUCING THE SAME, AND NEAR INFRARED ABSORBENT COMPRISING THE SAME

(75) Inventors: Hiroshi Terao, Osaka (JP); Shigeo Fujita, Kawachinagano (JP); Yojiro Kumagae, Kawachinagano (JP)

(73) Assignee: Yamamoto Chemicals, Inc., Osaka (JP)

( * ) Notice: Subject to any disclaimer, the term of this patent is extended or adjusted under 35 U.S.C. 154(b) by 0 days.

(21) Appl. No.: 09/673,029

(22) PCT Filed: Mar. 29, 2000

(86) PCT No.: PCT/JP00/01927

§ 371 (c)(1),
(2), (4) Date: Oct. 10, 2000

(87) PCT Pub. No.: WO00/60014

PCT Pub. Date: Oct. 12, 2000

(30) Foreign Application Priority Data

Mar. 30, 1999 (JP) .............................................. 11-129025

(51) Int. Cl.[7] .......................... G03F 7/038; C09B 47/22; B41N 1/14; C09K 3/00; C09D 513/22

(52) U.S. Cl. ................................. 430/270.1; 430/271.1; 430/302; 252/587; 540/122; 540/125; 540/139; 540/140; 540/142

(58) Field of Search .................................. 540/122, 125, 540/139, 140, 142; 430/272.1, 270.1; 252/587

(56) References Cited

U.S. PATENT DOCUMENTS

| 5,788,914 A | * | 8/1998 | Oi et al. ...................... 252/587 |
| 5,804,102 A | | 9/1998 | Oi et al. ...................... 252/587 |
| 5,919,600 A | * | 7/1999 | Huang et al. ............ 430/272.1 |

FOREIGN PATENT DOCUMENTS

| EP | A1782164 | 7/1997 |
| JP | A1078509 | 3/1998 |

* cited by examiner

*Primary Examiner*—Cynthia Hamilton
(74) *Attorney, Agent, or Firm*—Birch, Stewart, Kolasch & Birch, LLP (57) ABSTRACT

The invention relates to a novel phthalocyanine compound which absorbs in a near-infrared region of 700~1000 nm with little absorption in the visible region of the spectrum and can be applied with advantage to a near-infrared light-absorbing filter for plasma display, a secret ink and other applications and to a process for producing the phthalocyanine compound.

The above phthalocyanine compound has the following general formula (I). A near-infrared light-absorbing material containing the same is also provided.

(I)

wherein $R_1$~$R_8$ represents alkyl or alkoxyalkyl; $X_1$~$X_8$ represents sulfur or >$NR_9$; $X_1$=(either $X_3$ or $X_4$)=(either $X_5$ or $X_6$)=(either $X_7$ or $X_8$)=sulfur and $X_2$=(the other one of $X_3$ and $X_4$)=(the other one of $X_5$ and $X_6$)=(the other one of $X_7$ and $X_8$)=>$NR_9$; $R_9$ represents an acyl group which may optionally be substituted or an aroyl group which may optionally be substituted; M represents a couple of hydrogen atoms, a divalent metal, a trivalent metal derivative or a tetravalent metal derivative).

14 Claims, 3 Drawing Sheets

PHTHALOCYANINE COMPOUNDS, PROCESS FOR PRODUCING THE SAME, AND NEAR INFRARED ABSORBENT COMPRISING THE SAME

This application is the national phase under 35 U.S.C. § 371 of PCT International Application No. PCT/JP00/01927 which has an International filing date of Mar. 29, 2000, which designated the United States of America.

TECHNICAL FIELD

The present invention relates to a novel phthalocyanine compound, a process for producing the compound, and use of the compound.

More particularly, the present invention relates to a novel phthalocyanine compound absorbing in the near-infrared region of 700~1000 nm of the spectrum and useful for information recording systems utilizing laser light (such as optical cards, organic photoconductors, laser thermal transfer recording, laser thermal recording, laser direct printing plate making, etc.) and devices required to have near-infrared light absorbing properties (such as near-infrared light-absorbing filter, thermal-ray screening film, protective goggles, secret ink, agricultural film, etc.) and to a process for producing the compound.

PRIOR ART

Certain phthalocyanine compounds have good near-infrared absorbing properties and, therefore, there is a mounting interest in the application thereof to optical cards, near-infrared light-absorbing filters, thermal-ray screening film, protective goggles, laser direct printing plate making, laser thermal transfer recording, laser thermal recording, organic photoconductors for laser printer, etc.

The following compounds A and B are described in Example 13 and Example 20, respectively, in Tokkyo Kokai Koho (Japanese laid-open patent gazette) H8-60008.

Compound A

Compound B

However, these compounds A and B absorb not only in the near-infrared region but also in the visible region of the spectrum so that the scope of their application is limited. For example, in the field of the near-infrared light-absorbing filter for plasma display, secrete ink, etc., there exists a demand for a phthalocyanine compound which absorbs much in the near-infrared region and very little in the visible region of the spectrum (500–600 nm in particular).

OBJECT AND SUMMARY OF THE INVENTION

The present invention has for its object to provide a phthalocyanine compound which absorbs in the wavelength region of 700~1000 nm and satisfies the requirements of said various applications. The present invention has for another object to provide a process for producing said phthalocyanine compound in high yield.

The inventors of the present invention did much research for overcoming the above-mentioned disadvantages and found that these disadvantages can be overcome by a phthalocyanine compound having an acyl or aroyl group introduced onto the nitrogen atom on each benzothiazine ring of the phthalocyanine nucleus.

The present invention, in the first aspect thereof, is directed to a phthalocyanine compound of the following general formula (I).

(I)

wherein $R_1$, $R_2$, $R_3$, $R_4$, $R_5$, $R_6$, $R_7$ and $R_8$ each represents alkyl or alkoxyalkyl; $X_1$, $X_2$, $X_3$, $X_4$, $X_5$, $X_6$, $X_7$ and $X_8$ each represents sulfur or $>NR_9$; $X_1$=(either $X_3$ or $X_4$)=(either $X_5$ or $X_6$)=(either $X_7$ or $X_8$)=sulfur and $X_2$=(the other one of $X_3$ and $X_4$)=(the other one of X5 and $X_6$)=(the other one of $X_7$ and $X_8$)=>$NR_9$; $R_9$ represents an acyl group which may optionally be substituted or an aroyl group which may optionally be substituted; M represents a couple of hydrogen atoms, a divalent metal, a trivalent metal derivative or a tetravalent metal derivative).

The present invention relates, in a second aspect thereof, to a method of producing a phthalocyanine compound of the above general formula (I) which comprises reacting a phthalocyanine compound of general formula (II) with an acid anhydride of general formula (III) or an acid halide of general formula (IV).

(II)

wherein $R_1$~$R_8$ are as defined above; $Y_1$, $Y_2$, $Y_3$, $Y_4$, $Y_5$, $Y_6$, $Y_7$ and $Y_8$ each represents sulfur or $>NH$ and $Y_1$=(either $Y_3$ or $Y_4$)=(either $Y_5$ or $Y_6$)=(either $Y_7$ or $Y_8$)=sulfur and $Y_2$=(the other one of $Y_3$ and $Y_4$)=(the other one of $Y_5$ and $Y_6$)=(the other one of $Y_7$ and $Y_8$)=>NH; M represents a couple of hydrogen atoms, a divalent metal, a trivalent metal derivative or a tetravalent metal derivative.

$$(R_9)_2O \qquad (III)$$

wherein $R_9$ represents an acyl group which may optionally be substituted or an aroyl group which may optionally be substituted.

$$R_9X_9 \qquad (IV)$$

wherein $R_9$ is as defined above; $X_9$ represents halogen.

The present invention relates, in a third aspect thereof, to a near-infrared absorbing material comprising the phthalocyanine compound according to said first aspect of the present invention.

The present invention relates, in a fourth aspect thereof, to an original plate for direct printing plate making which comprises a photothermal conversion layer containing the phthalocyanine compound according to said first aspect of the invention as disposed on a support.

DISCLOSURE OF INVENTION

The present invention is now described in detail.

[Phthalocyanine compound]

In the first place, the phthalocyanine compound of the following general formula (I) according to the first aspect of the invention is described below.

(I)

wherein $R_{1\sim R8}$, $X_1\sim X_8$, and M are respectively as defined above.

When any of $R_1\sim R_8$ represents alkyl, it is preferably a straight-chain or branched alkyl group of 1~12 carbon atoms and more preferably a straight-chain or branched alkyl group of 1~8 carbon atoms. Examples include methyl, ethyl, n-propyl, isopropyl, n-butyl, isobutyl, sec-butyl, n-pentyl, isopentyl, neopentyl, n-hexyl, isohexyl, sec-hexyl, 2-ethylbutyl, n-heptyl, isoheptyl, sec-heptyl, n-octyl, 2-ethylhexyl and n-decyl, among others.

When any of $R_1\sim R_8$ represents alkoxyalkyl, it is preferably a group containing a total of 2 to 12 carbon atoms, more preferably a group containing a total of 3~6 carbon atoms, thus including methoxymethyl, methoxyethyl, methoxypropyl, methoxybutyl, ethoxyethyl, ethoxypropyl, ethoxybutyl, n-propoxyethyl, iso-propoxyethyl, n-propoxypropyl, n-butoxyethyl, iso-butoxypropyl, n-butoxybutyl, n-pentyloxypentyl, and n-hexyloxyhexyl, among others.

When $R_9$ represents an acyl group, it is preferably an optionally substituted acyl group containing a total of 2~18 carbon atoms. As specific examples, there can be mentioned acetyl, propionyl, butyryl, iso-butyryl, valeryl, iso-valeryl, trimethylacetyl, hexanoyl, heptanoyl, octanoyl, 2-ethylhexanoyl, nonanoyl, decanoyl, undecanoyl, lauroyl, tridecanoyl, tetradecanoyl, palmitoyl, hexadecanoyl, heptadecanoyl, stearoyl, oleoyl, octadecanoyl, trifluoroacetyl, pentafluoropropionyl, perfluorooctanoyl, 6-chlorohexanoyl, 6-bromohexanoyl, methoxyacetyl, 3,6-dioxaheptanoyl, etc. Particularly, acetyl, propionyl, butyryl, iso-butyryl, valeryl, iso-valeryl and trifluoroacetyl are preferred.

When $R_9$ represents an aroyl group, it is preferably an optionally substituted aroyl group containing a total of 7~12 carbon atoms. As specific examples, benzoyl, o-toluoyl, m-toluoyl, p-toluoyl, O-chlorobenzoyl, m-chlorobenzoyl, p-chlorobenzoyl, o-fluorobenzoyl, m-fluorobenzoyl, p-fluorobenzoyl, o-acetylbenzoyl, m-acetylbenzoyl, p-acetylbenzoyl, o-methoxybenzoyl, m-methoxybenzoyl, p-methoxybenzoyl, pentafluorobenzoyl, p-(trifluoromethyl)benzoyl, 1-naphthoyl, 2-naphthoyl, etc. can be mentioned. Particularly preferred are benzoyl, p-toluoyl, p-fluorobenzoyl and p-acetylbenzoyl.

When M represents a divalent metal, it is preferably Cu, Zn, Fe, Co, Ni, Ru, Pb, Rh, Pd, Pt, Mn, Sn or Nb. The trivalent or tetravalent metal derivative is preferably AlCl, InCl, FeCl, MnOH, $SiCl_2$, $SnCl_2$, $GeCl_2$, $Si(OH)_2$, $Sn(OH)_2$, $Ge(OH)_2$, VO or TiO. In particular, M is preferably Cu, Zn, Co, Ni, Pd, Pb, MnOH, AlCl, FeCl, InCl, $SnCl_2$, VO, or TiO.

Table 1 is a list of species of the phthalocyanine compound of general formula (I) which are preferred but not exclusive for use in the present invention.

The compounds shown in Table 1 are those compounds of formula (I) wherein $R_1$=(either $R_3$ or $R_4$)=(either $R_5$ or $R_6$)=(either $R_7$ or $R_8$) and $R_2$=(the other one of $R_3$ and $R_4$)=(the other one of $R_5$ and $R_6$)=(the other one of $R_7$ and $R_8$).

Compound Nos.

| | M | $R_1$ | $R_2$ | $R_9$ |
|---|---|---|---|---|
| (1) | Cu | $CH_3$ | $CH_3$ | $CH_3CO$ |
| (2) | Cu | $CH_3$ | $CH_3$ | $n\text{-}C_3H_7CO$ |
| (3) | Cu | $CH_3$ | $CH_3$ | $C_6H_5CO$ |
| (4) | Cu | $C_2H_5$ | $C_2H_5$ | $n\text{-}C_5H_{11}CO$ |
| (5) | VO | $C_2H_5$ | $C_2H_5$ | $C_2H_5CO$ |
| (6) | Zn | $C_2H_5$ | $C_2H_5$ | $CF_3CO$ |
| (7) | Cu | $n\text{-}C_3H_7$ | $n\text{-}C_3H_7$ | $iso\text{-}C_3H_7CO$ |
| (8) | Cu | $n\text{-}C_3H_7$ | $n\text{-}C_3H_7$ | $p\text{-}ClC_6H_4CO$ |
| (9) | Pb | $n\text{-}C_3H_7$ | $n\text{-}C_3H_7$ | $n\text{-}C_8H_{17}CO$ |
| (10) | Cu | $iso\text{-}C_3H_7$ | $iso\text{-}C_3H_7$ | $n\text{-}C_5H_{11}CO$ |
| (11) | VO | $iso\text{-}C_3H_7$ | $iso\text{-}C_3H_7$ | $CH_3CO$ |
| (12) | Co | $iso\text{-}C_3H_7$ | $iso\text{-}C_3H_7$ | $n\text{-}C_{17}H_{31}CO$ |
| (13) | Zn | $n\text{-}C_4H_9$ | $n\text{-}C_4H_9$ | $CH_3CO$ |
| (14) | FeCl | $n\text{-}C_4H_9$ | $n\text{-}C_4H_9$ | $o\text{-}CH_3C_6H_4CO$ |
| (15) | Co | $n\text{-}C_4H_9$ | $n\text{-}C_4H_9$ | $C_2H_5CO$ |
| (16) | Ni | $n\text{-}C_4H_9$ | $n\text{-}C_4H_9$ | $iso\text{-}C_4H_9CO$ |
| (17) | Pd | $n\text{-}C_4H_9$ | $n\text{-}C_4H_9$ | $n\text{-}C_6H_{13}CO$ |
| (18) | MnOH | $iso\text{-}C_4H_9$ | $iso\text{-}C_4H_9$ | $CF_3CO$ |
| (19) | VO | $iso\text{-}C_4H_9$ | $iso\text{-}C_4H_9$ | $n\text{-}C_3H_7CO$ |
| (20) | Ru | $iso\text{-}C_4H_9$ | $iso\text{-}C_4H_9$ | $C_2H_5CO$ |
| (21) | Rh | $iso\text{-}C_4H_9$ | $iso\text{-}C_4H_9$ | $n\text{-}C_4H_9CO$ |
| (22) | Pt | $iso\text{-}C_4H_9$ | $iso\text{-}C_4H_9$ | $n\text{-}C_5H_{11}CO$ |
| (23) | AlCl | $sec\text{-}C_4H_9$ | $sec\text{-}C_4H_9$ | $p\text{-}CF_3C_6H_4CO$ |
| (24) | InCl | $sec\text{-}C_4H_9$ | $sec\text{-}C_4H_9$ | $CH_3CO$ |
| (25) | Zn | $sec\text{-}C_4H_9$ | $sec\text{-}C_4H_9$ | $C_2H_5CO$ |
| (26) | Ni | $sec\text{-}C_4H_9$ | $sec\text{-}C_4H_9$ | $n\text{-}C_4H_9CO$ |
| (27) | FeCl | $sec\text{-}C_4H_9$ | $sec\text{-}C_4H_9$ | $n\text{-}C_{12}H_{25}CO$ |
| (28) | $SiCl_2$ | $n\text{-}C_5H_{11}$ | $n\text{-}C_5H_{11}$ | 1-naphthoyl |
| (29) | Cu | $n\text{-}C_5H_{11}$ | $n\text{-}C_5H_{11}$ | $iso\text{-}C_3H_7CO$ |
| (30) | TiO | $n\text{-}C_5H_{11}$ | $n\text{-}C_5H_{11}$ | m-$CH_3COC_6H_4CO$ |
| (31) | VO | $n\text{-}C_5H_{11}$ | $n\text{-}C_5H_{11}$ | $CH_3CO$ |
| (32) | Pd | $n\text{-}C_5H_{11}$ | $n\text{-}C_5H_{11}$ | $n\text{-}C_{18}H_{37}CO$ |
| (33) | VO | $iso\text{-}C_5H_{11}$ | $iso\text{-}C_5H_{11}$ | $CH_3CO$ |
| (34) | Cu | $iso\text{-}C_5H_{11}$ | $iso\text{-}C_5H_{11}$ | $CH_3CO$ |
| (35) | Zn | $iso\text{-}C_5H_{11}$ | $iso\text{-}C_5H_{11}$ | $m\text{-}FC_6H_4CO$ |
| (36) | FeCl | $iso\text{-}C_5H_{11}$ | $iso\text{-}C_5H_{11}$ | $p\text{-}CH_3OC_6H_4CO$ |
| (37) | Co | $iso\text{-}C_5H_{11}$ | $iso\text{-}C_5H_{11}$ | $C_6F_5CO$ |
| (38) | Ni | $iso\text{-}C_5H_{11}$ | $iso\text{-}C_5H_{11}$ | $CH_3CO$ |
| (39) | Pd | $iso\text{-}C_5H_{11}$ | $iso\text{-}C_5H_{11}$ | $CH_3CO$ |
| (40) | MnOH | $iso\text{-}C_5H_{11}$ | $iso\text{-}C_5H_{11}$ | $CH_3CO$ |
| (41) | Cu | $iso\text{-}C_5H_{11}$ | $iso\text{-}C_5H_{11}$ | $CH_3CO$ |
| (42) | VO | $iso\text{-}C_5H_{11}$ | $iso\text{-}C_5H_{11}$ | $C_2H_5CO$ |
| (43) | Cu | $iso\text{-}C_5H_{11}$ | $iso\text{-}C_5H_{11}$ | $C_2H_5CO$ |
| (44) | Zn | $iso\text{-}C_5H_{11}$ | $iso\text{-}C_5H_{11}$ | $C_2H_5CO$ |
| (45) | Pb | $iso\text{-}C_5H_{11}$ | $iso\text{-}C_5H_{11}$ | $C_2H_5CO$ |
| (46) | VO | $iso\text{-}C_5H_{11}$ | $iso\text{-}C_5H_{11}$ | $n\text{-}C_3H_7CO$ |
| (47) | Cu | $iso\text{-}C_5H_{11}$ | $iso\text{-}C_5H_{11}$ | $n\text{-}C_3H_7CO$ |
| (48) | Pd | $iso\text{-}C_5H_{11}$ | $iso\text{-}C_5H_{11}$ | $n\text{-}C_3H_7CO$ |
| (49) | MnOH | $iso\text{-}C_5H_{11}$ | $iso\text{-}C_5H_{11}$ | $n\text{-}C_3H_7CO$ |
| (50) | Vo | $iso\text{-}C_5H_{11}$ | $iso\text{-}C_5H_{11}$ | $iso\text{-}C_4H_9CO$ |
| (51) | Co | $iso\text{-}C_5H_{11}$ | $iso\text{-}C_5H_{11}$ | $n\text{-}C_4H_9CO$ |
| (52) | Ru | $iso\text{-}C_5H_{11}$ | $iso\text{-}C_5H_{11}$ | $n\text{-}C_6H_{13}CO$ |
| (53) | $SnCl_2$ | $n\text{-}C_6H_{13}$ | $n\text{-}C_6H_{13}$ | $CH_3CO$ |
| (54) | Zn | $n\text{-}C_6H_{13}$ | $n\text{-}C_6H_{13}$ | $CH_3CO$ |
| (55) | Pt | $n\text{-}C_6H_{13}$ | $n\text{-}C_6H_{13}$ | $n\text{-}C_3H_7CO$ |
| (56) | Ni | $n\text{-}C_6H_{13}$ | $n\text{-}C_6H_{13}$ | $n\text{-}C_5H_{11}CO$ |

-continued

| Compound Nos. | | | |
|---|---|---|---|
| M | $R_1$ | $R_2$ | $R_9$ |
| (57) Pd | $n\text{-}C_6H_{13}$ | $n\text{-}C_6H_{13}$ | $n\text{-}C_6H_{13}CO$ |
| (58) $GeCl_2$ | $iso\text{-}C_6H_{13}$ | $iso\text{-}C_6H_{13}$ | 2-naphthoyl |
| (59) FeCl | $iso\text{-}C_6H_{13}$ | $iso\text{-}C_6H_{13}$ | $CH_3CO$ |
| (60) Cu | $iso\text{-}C_6H_{13}$ | $iso\text{-}C_6H_{13}$ | $C_2H_5CO$ |
| (61) VO | $iso\text{-}C_6H_{13}$ | $iso\text{-}C_6H_{13}$ | $n\text{-}C_4H_9CO$ |
| (62) Zn | $iso\text{-}C_6H_{13}$ | $iso\text{-}C_6H_{13}$ | $C_6H_5CO$ |
| (63) $Si(OH)_2$ | $n\text{-}C_7H_{15}$ | $n\text{-}C_7H_{15}$ | $C_6H_5CO$ |
| (64) Rh | $n\text{-}C_7H_{15}$ | $n\text{-}C_7H_{15}$ | $CH_3CO$ |
| (65) Zn | $n\text{-}C_7H_{15}$ | $n\text{-}C_7H_{15}$ | $n\text{-}C_3H_7CO$ |
| (66) Ni | $n\text{-}C_7H_{15}$ | $n\text{-}C_7H_{15}$ | $iso\text{-}C_4H_9CO$ |
| (67) Co | $n\text{-}C_7H_{15}$ | $n\text{-}C_7H_{15}$ | $n\text{-}C_5H_{11}CO$ |
| (68) $Sn(OH)_2$ | $iso\text{-}C_7H_{15}$ | $iso\text{-}C_7H_{15}$ | $CH_3CO$ |
| (69) MnOH | $iso\text{-}C_7H_{15}$ | $iso\text{-}C_7H_{15}$ | $C_2H_5CO$ |
| (70) TiO | $iso\text{-}C_7H_{15}$ | $iso\text{-}C_7H_{15}$ | $iso\text{-}C_3H_7CO$ |
| (71) Pb | $iso\text{-}C_7H_{15}$ | $iso\text{-}C_7H_{15}$ | $n\text{-}C_5H_{11}CO$ |
| (72) Mg | $iso\text{-}C_7H_{15}$ | $iso\text{-}C_7H_{15}$ | $n\text{-}C_{12}H_{25}CO$ |
| (73) Cu | $n\text{-}C_8H_{17}$ | $n\text{-}C_8H_{17}$ | $CH_3CO$ |
| (74) $Ge(OH)_2$ | $n\text{-}C_8H_{17}$ | $n\text{-}C_8H_{17}$ | $n\text{-}C_3H_7CO$ |
| (75) InCl | $n\text{-}C_8H_{17}$ | $n\text{-}C_8H_{17}$ | oleoyl |
| (76) Zn | $n\text{-}C_8H_{17}$ | $n\text{-}C_8H_{17}$ | $C_6H_5CO$ |
| (77) FeCl | $n\text{-}C_8H_{17}$ | $n\text{-}C_8H_{17}$ | $m\text{-}CH_3OC_6H_4CO$ |
| (78) Cu | $n\text{-}C_{10}H_{21}$ | $n\text{-}C_{10}H_{21}$ | $CH_3CO$ |
| (79) VO | $n\text{-}C_{10}H_{21}$ | $n\text{-}C_{10}H_{21}$ | $CH_3CO$ |
| (80) Ni | $n\text{-}C_{10}H_{21}$ | $n\text{-}C_{10}H_{21}$ | $n\text{-}C_3H_7CO$ |
| (81) Co | $n\text{-}C_{10}H_{21}$ | $n\text{-}C_{10}H_{21}$ | $iso\text{-}C_3H_7CO$ |
| (82) FeCl | $n\text{-}C_{10}H_{21}$ | $n\text{-}C_{10}H_{21}$ | $C_6H_5CO$ |
| (83) Cu | $iso\text{-}C_{10}H_{21}$ | $iso\text{-}C_{10}H_{21}$ | $iso\text{-}C_3H_7CO$ |
| (84) Zn | $iso\text{-}C_{10}H_{21}$ | $iso\text{-}C_{10}H_{21}$ | $CH_3CO$ |
| (85) Pd | $iso\text{-}C_{10}H_{21}$ | $iso\text{-}C_{10}H_{21}$ | $p\text{-}FC_6H_4CO$ |
| (86) MnO | $iso\text{-}C_{10}H_{21}$ | $iso\text{-}C_{10}H_{21}$ | $n\text{-}C_{12}H_{25}CO$ |
| (87) VO | $iso\text{-}C_{10}H_{21}$ | $iso\text{-}C_{10}H_{21}$ | $CH_3CO$ |
| (88) Cu | $n\text{-}C_{12}H_{25}$ | $n\text{-}C_{12}H_{25}$ | $CF_3CO$ |
| (89) Ru | $n\text{-}C_{12}H_{25}$ | $n\text{-}C_{12}H_{25}$ | $CH_3CO$ |
| (90) VO | $n\text{-}C_{12}H_{25}$ | $n\text{-}C_{12}H_{25}$ | $C_2H_5CO$ |
| (91) VO | $n\text{-}C_{12}H_{25}$ | $n\text{-}C_{12}H_{25}$ | $iso\text{-}C_3H_7CO$ |
| (92) VO | $n\text{-}C_{12}H_{25}$ | $n\text{-}C_{12}H_{25}$ | $n\text{-}C_5H_{11}CO$ |
| (93) Ni | $iso\text{-}C_{12}H_{25}$ | $iso\text{-}C_{12}H_{25}$ | $CH_3CO$ |
| (94) Zn | $iso\text{-}C_{12}H_{25}$ | $iso\text{-}C_{12}H_{25}$ | $C_6H_5CO$ |
| (95) VO | $iso\text{-}C_{12}H_{25}$ | $iso\text{-}C_{12}H_{25}$ | $o\text{-}FC_6H_4CO$ |
| (96) Cu | $iso\text{-}C_{12}H_{25}$ | $iso\text{-}C_{12}H_{25}$ | $CF_3CO$ |
| (97) Pb | $iso\text{-}C_{12}H_{25}$ | $iso\text{-}C_{12}H_{25}$ | $n\text{-}C_7H_{15}CO$ |
| (98) Cu | $CH_3OC_2H_4$ | $CH_3OC_2H_4$ | $CH_3CO$ |
| (99) Zn | $CH_3OC_2H_4$ | $CH_3OC_2H_4$ | $CH_3CO$ |
| (100) VO | $CH_3OC_2H_4$ | $CH_3OC_2H_4$ | $CH_3CO$ |
| (101) Co | $CH_3OC_2H_4$ | $CH_3OC_2H_4$ | $CH_3CO$ |
| (102) Ni | $CH_3OC_2H_4$ | $CH_3OC_2H_4$ | $CF_3CO$ |
| (103) Pd | $CH_3OC_2H_4$ | $CH_3OC_2H_4$ | $CF_3CO$ |
| (104) MnOH | $CH_3OC_2H_4$ | $CH_3OC_2H_4$ | $CF_3CO$ |
| (105) VO | $CH_3OC_2H_4$ | $CH_3OC_2H_4$ | $CF_3CO$ |
| (106) TiO | $CH_3OC_2H_4$ | $CH_3OC_2H_4$ | $CF_3CO$ |
| (107) AlCl | $CH_3OC_2H_4$ | $CH_3OC_2H_4$ | $C_2H_5CO$ |
| (108) InCl | $CH_3OC_2H_4$ | $CH_3OC_2H_4$ | $n\text{-}C_3H_7CO$ |
| (109) MnOH | $CH_3OC_2H_4$ | $CH_3OC_2H_4$ | $n\text{-}C_5H_{11}CO$ |
| (110) VO | $CH_3OC_3H_6$ | $CH_3OC_3H_6$ | $CH_3CO$ |
| (111) Pd | $CH_3OC_3H_6$ | $CH_3OC_3H_6$ | $CF_3CO$ |
| (112) Zn | $CH_3OC_3H_6$ | $CH_3OC_3H_6$ | $C_2H_5CO$ |
| (113) FeCl | $CH_3OC_3H_6$ | $CH_3OC_3H_6$ | $n\text{-}C_6H_{13}CO$ |
| (114) Co | $CH_3OC_3H_6$ | $CH_3OC_3H_6$ | stearoyl |
| (115) Ni | $CH_3OC_4H_8$ | $CH_3OC_4H_8$ | $CH_3CO$ |
| (116) Cu | $CH_3OC_4H_8$ | $CH_3OC_4H_8$ | $CH_3CO$ |
| (117) Pb | $CH_3OC_4H_8$ | $CH_3OC_4H_8$ | $C_2H_5CO$ |
| (118) Ru | $CH_3OC_4H_8$ | $CH_3OC_4H_8$ | $n\text{-}C_3H_7CO$ |
| (119) Rh | $CH_3OC_4H_8$ | $CH_3OC_4H_8$ | $n\text{-}C_{13}H_{27}CO$ |
| (120) VO | $C_2H_5OC_2H_4$ | $C_2H_5OC_2H_4$ | $CH_3CO$ |
| (121) Ru | $C_2H_5OC_2H_4$ | $C_2H_5OC_2H_4$ | $CH_3CO$ |
| (122) Rh | $C_2H_5OC_2H_4$ | $C_2H_5OC_2H_4$ | $p\text{-}CH_3C_6H_4CO$ |
| (123) Pd | $C_2H_5OC_2H_4$ | $C_2H_5OC_2H_4$ | $o\text{-}CH_3C_6H_4CO$ |
| (124) Pt | $C_2H_5OC_2H_4$ | $C_2H_5OC_2H_4$ | $n\text{-}C_6H_{13}CO$ |
| (125) $SiCl_2$ | $n\text{-}C_3H_7OC_2H_4$ | $n\text{-}C_3H_7OC_2H_4$ | $CH_3CO$ |
| (126) Cu | $n\text{-}C_3H_7OC_2H_4$ | $n\text{-}C_3H_7OC_2H_4$ | $CH_3CO$ |
| (127) Zn | $n\text{-}C_3H_7OC_2H_4$ | $n\text{-}C_3H_7OC_2H_4$ | $m\text{-}CH_3OC_6H_4CO$ |
| (128) FeCl | $iso\text{-}C_3H_7OC_2H_4$ | $iso\text{-}C_3H_7OC_2H_4$ | $n\text{-}C_3H_7CO$ |
| (129) Co | $iso\text{-}C_3H_7OC_2H_4$ | $iso\text{-}C_3H_7OC_2H_4$ | $n\text{-}C_5H_{11}CO$ |

-continued

| Compound Nos. | | | |
|---|---|---|---|
| M | $R_1$ | $R_2$ | $R_9$ |
| (130) MnOH | $C_2H_5OC_3H_6$ | $C_2H_5OC_3H_6$ | $o\text{-}CH_3COC_6H_4CO$ |
| (131) VO | $C_2H_5OC_3H_6$ | $C_2H_5OC_3H_6$ | $CH_3CO$ |
| (132) TiO | $C_2H_5OC_3H_6$ | $C_2H_5OC_3H_6$ | $C_2H_5CO$ |
| (133) AlCl | $C_2H_5OC_3H_6$ | $C_2H_5OC_3H_6$ | $n\text{-}C_4H_9CO$ |
| (134) InCl | $C_2H_5OC_3H_6$ | $C_2H_5OC_3H_6$ | $n\text{-}C_6H_{13}CO$ |
| (135) Cu | $C_2H_5OC_4H_8$ | $C_2H_5OC_4H_8$ | $CH_3CO$ |
| (136) Cu | $C_2H_5OC_4H_8$ | $C_2H_5OC_4H_8$ | $C_2H_5CO$ |
| (137) Ni | $C_2H_5OC_4H_8$ | $C_2H_5OC_4H_8$ | $C_2H_5CO$ |
| (138) Zn | $C_2H_5OC_4H_8$ | $C_2H_5OC_4H_8$ | $iso\text{-}C_3H_7CO$ |
| (139) Co | $C_2H_5OC_4H_8$ | $C_2H_5OC_4H_8$ | $iso\text{-}C_5H_{11}CO$ |
| (140) Cu | $C_4H_9OC_4H_8$ | $C_4H_9OC_4H_8$ | $C_2H_5CO$ |
| (141) Pb | $C_4H_9OC_4H_8$ | $C_4H_9OC_4H_8$ | $n\text{-}C_5H_{11}CO$ |
| (142) Ru | $C_4H_9OC_4H_8$ | $C_4H_9OC_4H_8$ | $C_2H_5CO$ |
| (143) Rh | $C_4H_9OC_4H_8$ | $C_4H_9OC_4H_8$ | $CH_3CO$ |
| (144) VO | $C_4H_9OC_6H_{12}$ | $C_4H_9OC_6H_{12}$ | $C_2H_5CO$ |
| (145) Zn | $C_4H_9OC_6H_{12}$ | $C_4H_9OC_6H_{12}$ | $iso\text{-}C_5H_{11}CO$ |
| (146) FeCl | $C_4H_9OC_6H_{12}$ | $C_4H_9OC_6H_{12}$ | $C_2F_5CO$ |
| (147) Tio | $C_4H_9OC_6H_{12}$ | $C_4H_9OC_6H_{12}$ | $iso\text{-}C_5H_{11}CO$ |
| (148) AlCl | $C_6H_{13}OC_6H_{12}$ | $C_6H_{13}OC_6H_{12}$ | $C_2H_5CO$ |
| (149) VO | $C_6H_{13}OC_6H_{12}$ | $C_6H_{13}OC_6H_{12}$ | $n\text{-}C_9H_{19}CO$ |
| (150) Cu | $C_6H_{13}OC_6H_{12}$ | $C_6H_{13}OC_6H_{12}$ | $C_2H_5CO$ |
| (151) Co | $C_6H_{13}OC_6H_{12}$ | $C_6H_{13}OC_6H_{12}$ | $C_2F_5CO$ |
| (152) Cu | $C_2H_5$ | $n\text{-}C_3H_7$ | $CH_3CO$ |
| (153) VO | $C_2H_5$ | $n\text{-}C_3H_7$ | $CH_3CO$ |
| (154) Cu | $C_2H_5$ | $n\text{-}C_4H_9$ | $CH_3CO$ |
| (155) VO | $C_2H_5$ | $n\text{-}C_4H_9$ | $CH_3CO$ |
| (156) Cu | $C_2H_5$ | $n\text{-}C_6H_{13}$ | $C_2H_5CO$ |
| (157) Cu | $C_2H_5$ | $n\text{-}C_7H_{15}$ | $n\text{-}C_4H_9CO$ |
| (158) Cu | $C_2H_5$ | $n\text{-}C_8H_{17}$ | $n\text{-}C_6H_{13}CO$ |
| (159) Ni | $iso\text{-}C_5H_{11}$ | $C_2H_5$ | $C_6H_5CO$ |
| (160) Co | $iso\text{-}C_5H_{11}$ | $n\text{-}C_4H_9$ | $CH_3CO$ |
| (161) Zn | $iso\text{-}C_5H_{11}$ | $n\text{-}C_6H_{13}$ | $C_2H_5CO$ |
| (162) VO | $iso\text{-}C_5H_{11}$ | $n\text{-}C_7H_{15}$ | $n\text{-}C_3H_7CO$ |
| (163) MnOH | $iso\text{-}C_5H_{11}$ | $n\text{-}C_8H_{17}$ | $n\text{-}C_8H_{17}CO$ |
| (164) Cu | $iso\text{-}C_5H_{11}$ | $CH_3OC_2H_4$ | $CH_3CO$ |
| (165) Zn | $iso\text{-}C_5H_{11}$ | $CH_3OC_2H_4$ | $CH_3CO$ |
| (166) FeCl | $iso\text{-}C_5H_{11}$ | $CH_3OC_2H_4$ | $CH_3CO$ |
| (167) Co | $iso\text{-}C_5H_{11}$ | $CH_3OC_2H_4$ | $CH_3CO$ |
| (168) Ni | $iso\text{-}C_5H_{11}$ | $CH_3OC_2H_4$ | $CH_3CO$ |
| (169) Pd | $iso\text{-}C_5H_{11}$ | $CH_3OC_2H_4$ | $CH_3CO$ |
| (170) MnOH | $iso\text{-}C_5H_{11}$ | $CH_3OC_2H_4$ | $CH_3CO$ |
| (171) VO | $iso\text{-}C_5H_{11}$ | $CH_3OC_2H_4$ | $CH_3CO$ |
| (172) Cu | $iso\text{-}C_5H_{11}$ | $CH_3OC_3H_6$ | $CH_3CO$ |
| (173) VO | $iso\text{-}C_5H_{11}$ | $CH_3OC_3H_6$ | $CH_3CO$ |
| (174) AlCl | $iso\text{-}C_5H_{11}$ | $CH_3OC_4H_8$ | $C_2H_5CO$ |
| (175) InCl | $iso\text{-}C_5H_{11}$ | $C_2H_5OC_2H_4$ | $n\text{-}C_3H_7CO$ |
| (176) Ni | $iso\text{-}C_5H_{11}$ | $C_2H_5OC_4H_8$ | $n\text{-}C_5H_{11}CO$ |
| (177) $H_2$ | $iso\text{-}C_5H_{11}$ | $iso\text{-}C_5H_{11}$ | $CH_3CO$ |

[Production of the Phthalocyanine Compound]

The phthalocyanine compound of general formula (I) according to the present invention can be produced by reacting a phthalocyanine compound of the following general formula (II) with an acid anhydride of the following general formula (III) or an acid halide of the following general formula (IV) in a suitable solvent.

(II)

wherein $R_1 \sim R_8$, $Y_1 \sim Y_8$ and M are respectively as defined above.

$(R_9)_2O$         (III)

wherein $R_9$ represents an acyl group which may optionally be substituted or an aroyl group which may optionally be substituted.

$R_9X_9$         (IV)

wherein $R_9$ is as defined above; $X_9$ represents halogen.

The acid anhydride of general formula (III) includes but is not limited to acetic anhydride, propionic anhydride, n-butyric anhydride, iso-butyric anhydride, n-valeric anhydride, isovaleric anhydride, hexanoic anhydride, heptanoic anhydride, octanoic anhydride, trifluoroacetic anhydride and benzoic anhydride. The acid halide of general formula (IV) includes but is not limited to acetyl chloride, acetyl bromide, ethylcarbonyl chloride, decanecarbonyl chloride, lauryl chloride, stearyl chloride, oleyl chloride, benzoyl chloride, toluoyl chloride, methoxyacetyl chloride, trifluoromethylbenzoyl chloride and naphtoyl chloride. The level of use of the compound of general formula (III) or (IV) relative to the phthalocyanine compound of general formula (II) is 0.1~100 equivalents, preferably 4~20 equivalents.

The solvent for use in conducting the above reaction includes polar solvents such as pyridine, N,N-dimethylformamide, dimethyl acetamide, dimethyl sulfoxide, N,N'-dimethylimidazolidinone, sulfolane, etc. and aromatic hydrocarbons such as benzene, toluene, xylene, chlorobenzene, nitrobenzene, etc. Furthermore, tertiary amines such as triethylamine and inorganic acids such as sulfuric acid and phosphoric acid may also be added. The level of use of the solvent relative to the phthalocyanine comopund of general formula (II) is 1~100 parts by weight, preferably 5~20 parts by weight.

The reaction temperature may range from 0° C. to the reflux temperature of the solvent, preferably from 20° C. to the reflux temperature of the solvent.

The reaction time is preferably 30 minutes~72 hours, more preferably 2~24 hours.

After the reaction, the objective compound can be isolated by removing the solvent by distillation or treating the reaction mixture with a poor solvent for the phthalocyanine compound and collecting the precipitate by filtration. The product thus obtained can be further purified by recrystallization or column chromatography to give the objective compound of improved purity.

The starting material phthalocyanine compound of general formula (II) can be produced by the process described in JP Kokai H8-60008 and, in many cases, is obtained as a mixture of position isomers with respect to the relative positions of $R_1$ and $R_2$, $R_3$ and $R_4$, $R_5$ and $R_6$, and $R_7$ and $R_8$ (or $Y_1$ and $Y_2$, $Y_3$ and $Y_4$, $Y_5$ and $Y_6$, and $Y_7$ and $Y_8$).

[Near-infrared Light-absorbing Material]

The near-infrared light-absorbing material of the invention may contain a binder resin or the like in addition to -the phthalocyanine compound of general formula (I).

Furthermore, the near-infrared light-absorbing material of the invention can be implemented by using the phthalocyanine compound of general formula (I) in combination with various known near-infrared light-absorbing substances within the range not contrary to the objects of the invention.

The near-infrared light-absorbing materials mentioned above include not only a variety of pigments such as carbon black, aniline black, etc. but also other colors or dyes such as the polymethine dyes, phthalocyanine dyes, dithiol/dithiolane metal complex salt dyes, naphthoquinone/anthraquinone dyes, triphenylmethane (analog) dyes, aminium/diimmonium dyes, azo dyes, indoaniline metal complex dyes, intermolecular CT dyes, etc., all of which are described in "Near-Infrared Absorbing Colors" (P45~51), KAGAKU KOGYO (Chemical Industry) (May 1986 issue) and in Chapter 2-2.3 of "The Development and Market Trend of Functional Dyes in the Nineties", CMC (1990).

The binder resin is not particularly restricted in kind but includes the homopolymers and copolymers of acrylic monomers such as acrylic acid, methacrylic acid, acrylic esters, methacrylic esters, etc., cellulosic polymers such as methylcellulose, ethylcellulose, cellulose acetate, etc., vinyl polymers and vinyl copolymers such as polystyrene, vinyl chloride-vinyl acetate copolymer, polyvinyl-pyrrolidone, polyvinyl butyral, polyvinyl alcohol, etc., condensation polymers such as polyesters and polyamides, rubber-like thermoplastic polymers such as butadiene-styrene copolymer etc., and polymers available upon polymerization and crosslinking of photopolymerizable compounds such as epoxy compounds.

When the near-infrared light-absorbing material of the invention is applied to an optical recording medium such as an optical card, the objective product can be obtained by coating a glass, plastic resin or other substrate with a solution of the near-infrared light-absorbing material in an organic solvent by the spin coating or other known technique. The substrate resin which can be used is not particularly restricted but includes acrylic resin, polyethylene resin, vinyl chloride resin, vinylidene chloride resin and polycarbonate resin, among others. The solvent for the spin-coating or other coating procedure is not particularly restricted but includes hydrocarbons, halogenated hydrocarbons, ethers, ketones, alcohols and cellosolves, although alcoholic solvents such as methanol, ethanol, propanol, etc. and cellosolve series solvents such as methylcellosolve, ethylcellosolve, etc. are preferred.

When the near-infrared light-absorbing material of the invention is to be applied to a near-infrared light-absorbing filter, a heat-ray screening film, or an agricultural film, the objective product can be produced by mixing the near-infrared light absorbing material with a plastic resin, optionally together with an organic solvent, and molding the composition into a sheet or film in accordance with the hitherto-known or investigated technology, such as injection molding, casting or the like. The resin which can be used in this manner is not particularly restricted but includes acrylic resin, polyethylene resin, vinyl chloride resin, vinylidene chloride resin and polycarbonate resin, among others. The solvent mentioned just above is not particularly restricted but includes hydrocarbons, halogenated hydrocarbons, ethers, ketones, alcohols and cellosolves, etc.; although alcoholic solvents such as methanol, ethanol, propanol, etc. and cellosolve series solvents such as methylcellosolve, ethylcellosolve, etc. are preferred.

When the near-infrared light-absorbing material of the present invention is to be applied to a recording medium such as a laser thermal transfer recording material or a laser thermal recording material, it can be used as formulated with a chromogenic or coloring agent or, as an alternative, a discrete layer containing such a chromogenic or coloring agent may be provided. As the chromogenic or coloring agent, there can be employed sublimable dyes or pigments, electron-donating dye precursors and electron-accepting compounds, polymerizable polymers and various other substances capable of forming images by undergoing physical or chemical change in response to heat which are in use or under development. For example, the coloring agent which can be used in the laser thermal transfer recording material includes but is not limited to inorganic pigments such as titanium dioxide, carbon black, zinc oxide, Prussian blue, cadmium sulfide, iron oxide, and chromates of lead, zinc, barium, and calcium, and organic colors such as azo, thioindigo, anthraquinone, anthoanthrone, triphendioxane, phthalocyanine, quinacridone, and other dyes. As examples of the dye, acid dyes, direct dyes, dispersed dyes, oil-soluble dyes, and metal-containing oil-soluble dyes can be mentioned.

The chromogenic agent for use in the laser thermal recording material is not particularly restricted but any of the substances in use in the conventional thermal recording materials can be employed. The electron-donating dye precursor is a compound which donates an electron or accepts the proton of an acid or the like to develop a color and, as such, includes those compounds which have a partial structure such as a lactone, lactam, sultone, spiropyran, ester, or amide structure which undergoes ring-opening or cleavage upon contact with an electron-accepting compound. Thus, for example, triphenylmethane compounds, fluoran compounds, phenothiazine compounds, indolylphthalide compounds, leucoauramine compounds, rhodamine lactam compounds, triphenylmethane compounds, triazene compounds, spiropyran compounds, and fluorene compounds can be mentioned. The electron-accepting compound includes phenolic compounds, organic acids and salts thereof, hydroxybenzoic acid esters, and so forth.

[Original Plate for Direct Printing Plate Making]

The phthalocyanine compound of the present invention can be used with advantage as a light-to-heat converting agent for the original plate for direct printing plate making. The original plate for direct printing plate making comprises a photothermal conversion layer comprising such a light-to-heat converting agent as constructed on a support. Optionally, a silicone rubber layer may be formed on such a photothermal conversion layer and a protective layer or the like may be further superimposedly constructed.

As components of the photothermal conversion layer, there may be an image-forming component, binder resin component or the like in addition to the above phthalocyanine compound of the invention. Alternatively, a layer containing the image-forming component may be built up on the photothermal conversion layer.

The image-forming component is a material which, when heated, undergoes physical or chemical change to form an image and the variety of materials heretofore proposed or in use can be utilized. For example, the material containing a microencapsulated heat-fusible substance and a binder resin as disclosed in Japanese Kokai Tokkyo Koho H3-108588, the material comprising an active hydrogen-containing binder and a blocked isocyanate on the hydrophilic surface of a support as disclosed in Japanese Kokai Tokkyo Koho S62-164049, the material comprising a microencapsulated lipophilic component and a hydrophilic polymer binder as disclosed in Japanese Kokai Tokkyo Koho H7-1849, the material comprising an acid precursor, a vinyl ether-containing compound and an alkali-soluble resin as disclosed in Japanese Kokai Tokkyo Koho H8-220752, the material comprising a hydroxy-containing macromolecular compound and an o-naphthoquinone diazide compound as disclosed in Japanese Kokai Tokkyo Koho H9-5993, the material containing nitrocellulose etc. as disclosed in Japanese Kokai Tokkyo Koho H9-131977, the material comprising a polymerization initiator and an ethylenically unsaturated monomer, oligomer or macromonomer as disclosed in Japanese Kokai Tokkyo Koho H9-146264, among others. In certain applications, the objective image can be formed by constructing a silicone rubber layer on a photothermal conversion layer (light-sensitive layer or a heat-sensitive recording layer) and, after exposure, bringing the silicone layer into intimate contact or apart as described in Japanese Kokai Tokkyo Koho H9-80745, Kokai Tokkyo Koho H9-131977, and Kokai Tokkyo Koho H9-146264, for instance.

The binder resin to be used for the photothermal conversion layer is not particularly restricted in kind but includes the homopolymers and copolymers of acrylic monomers such as acrylic acid, methacrylic acid, acrylic esters, methacrylic esters, etc., cellulosic polymers such as methylcellulose, ethylcellulose, cellulose acetate, etc., vinyl polymers and vinyl copolymers such as polystyrene, vinyl chloride-vinyl acetate copolymer, polyvinylpyrrolidone., polyvinyl butyral, polyvinyl alcohol, etc., condensation polymers such as polyesters and polyamides, rubber-like thermoplastic polymers such as butadiene-styrene copolymer etc., and polymers available upon polymerization and crosslinking of photopolymerizable compounds such as epoxy compounds.

The original plate for direct printing plate making according to the present invention should have a sufficient degree of flexibility to permit setting on a conventional printing press and, at the same time, have a sufficient strength to withstand the load which may act on it during the printing process. The support, therefore, can be made from many kinds of materials such as paper, plastic (e.g. polyethylene, polypropylene, polystyrene, etc.)-laminated paper, metal sheets made from aluminum (inclusive of its alloys), zinc, copper, etc., and plastic films such as cellulose diacetate, cellulose triacetate, cellulose butyrate, polyethylene terephthalate, polyethylene, polystyrene, polypropylene, polycarbonate, polyvinyl acetate, etc. As representative supports, coated paper, aluminum or other metal sheets, polyethylene terephthalate or other plastic film, rubber, and their composites can be mentioned. The preferred support material includes aluminum, aluminum alloy, and plastic film. The thickness of the support is 25 $\mu$m~3 mm, preferably 100 $\mu$m~500 $\mu$m.

The usual process for fabricating an original plate comprises dispersing or dissolving the phthalocyanine compound, image-forming component, binder resin component or the like in a solvent such as an organic solvent and coating a support with the dispersion or solution.

The solvent which can be used in this process includes water, alcohols such as methyl alcohol, isopropyl alcohol, isobutyl alcohol, cyclopentanol, cyclohexanol, diacetone alcohol, etc., cellosolves such as methylcellosolve, ethylcellosolve, etc., aromatic hydrocarbons such as toluene, xylene, chlorobenzene, etc., esters such as ethyl acetate, butyl acetate, isoamyl acetate, methyl propionate, etc. ketones such as acetone, methyl ethyl ketone, methyl isobutyl ketone, cyclohexanone, etc., chlorinated hydrocarbons such as methylene chloride, chloroform, trichloroethylene, etc., ethers such as tetrahydrofuran, dioxane, etc., and aprotic polar solvents such as N,N-dimethylformamide, N-methylpyrrolidone, and so forth.

For improved adhesion and printing quality, a primer layer may be interposed between the support and the photothermal conversion layer or the support itself may be surface-treated. The primer layer may for example be a light-sensitive polymer layer photocured prior to construction of the near-infrared light-absorbing layer as disclosed in Japanese Kokai Tokkyo Koho S60-22903, the heat-cured epoxy resin layer disclosed in Japanese Kokai Tokkyo Koho S62-50760, the cured gelation film disclosed in Japanese Kokai Tokkyo Koho S63-133151, the layer formed by using a urethane resin and a silane coupling agent as disclosed in Japanese Kokai Tokkyo Koho H3-200965, and the urethane resin layer disclosed in Japanese Kokai Tokkyo Koho H3-273248.

To provide a protective film for the purpose of protecting the surface of said photothermal conversion layer or silicone rubber layer, a transparent film such as polyethylene, polypropylene, polyvinyl chloride, polyvinylidene chloride, polyvinyl alcohol, polyethylene terephthalate, or cellophane film may be laminated or such a film may be drawn and used.

EXAMPLES

The following examples illustrate the present invention in further detail without defining the scope of the invention.

Example 1
Synthesis of Compound (33)

A phthalocyanine compound of general formula (II) [$R_1=R_2=R_3=R_4=R_5=R_6=R_7=R_8$=iso-pentyl; $Y_1$=(either $Y_3$ or $Y_4$)=(either $Y_5$ or $Y_6$)=(either $Y_7$ or $Y_8$)=sulfur; $Y_2$=(the other one of $Y_3$ and $Y_4$)=(the other one of $Y_5$ and $Y_6$)=(the other one of $Y_7$ and $Y_8$)=>NH; M=VO] (5.0 g), acetic anhydride (2.4 g) and toluene (50 mL) were admixed, 2 drops of concentrated sulfuric acid was added, and the mixture was refluxed and stirred for 15 hours. After cooling, 100 ml of water was added to the reaction mixture and the toluene layer was separated, washed with hot water and filtered, and the solvent was distilled off. To the residue was added 50 ml of methanol, and the mixture was stirred under reflux for 1 hour. After cooling, the crystals formed were harvested by filtration and dried to give 5.2 g of compound (33) as green powders. This product was identified to be the objective compound based on the following analytical data.

The metal was analyzed by atomic absorption analysis.

Elemental analysis ($C_{104}H_{116}N_{12}O_{13}S_4V$):MW=1921.5

|  | C | H | N | V |
|---|---|---|---|---|
| Calcd. (%): | 65.01 | 6.09 | 8.75 | 2.65 |
| Found (%): | 64.97 | 6.11 | 8.68 | 2.7 |

$\lambda_{max}$: 803 nm (in toluene); $\epsilon g$: $1.04 \times 10^5$ ml/g·cm (in toluene).

Figure 1:
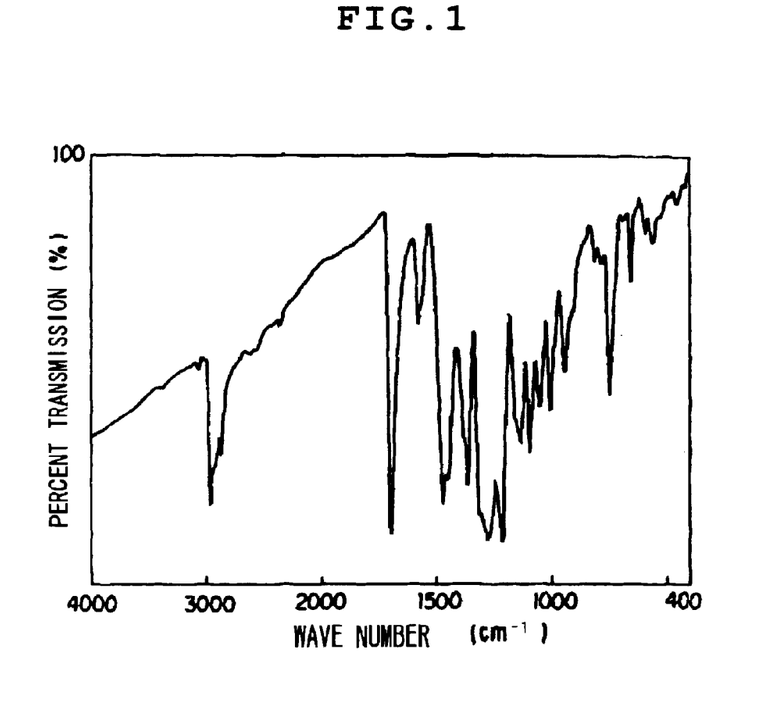
FIG. 1 is a Fourier transform infrared absorption spectrum of compound (33) in Example 1.

The FT-IR spectrum of the compound obtained is shown in FIG. 1.

Figure 2:
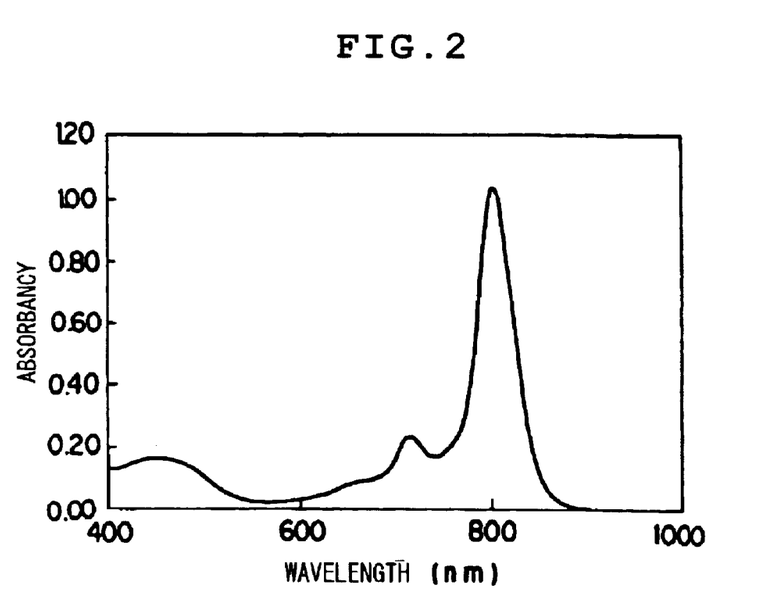
FIG. 2 is an absorption spectrum of compound (33) in Example 1 as measured in toluene.

The VIS-NIR absorption spectrum of the compound is shown in FIG. 2.

Example 2
Synthesis of Compound (46)

Except that 3.6 g of n-butyric anhydride was used in lieu of 2.4 g of acetic anhydride, the procedure of Example 1 was repeated to give 5.2 g of compound (46) as green powders.

The elemental analysis, absorption maxima ($\lambda_{max}$) and gram-absorption coefficient ($\epsilon g$) of this compound were as follows.

Elemental analysis ($C_{112}H_{132}N_{12}O_{13}S_4V$):MW=2033.5

|  | C | H | N | V |
|---|---|---|---|---|
| Calcd. (%): | 66.15 | 6.54 | 8.27 | 2.51 |
| Found (%): | 66.18 | 6.49 | 8.25 | 2.5 |

$\lambda_{max}$: 805 nm (in toluene); $\epsilon g$: $9.74 \times 10^4$ ml/g·cm (in toluene).

Figure 3:
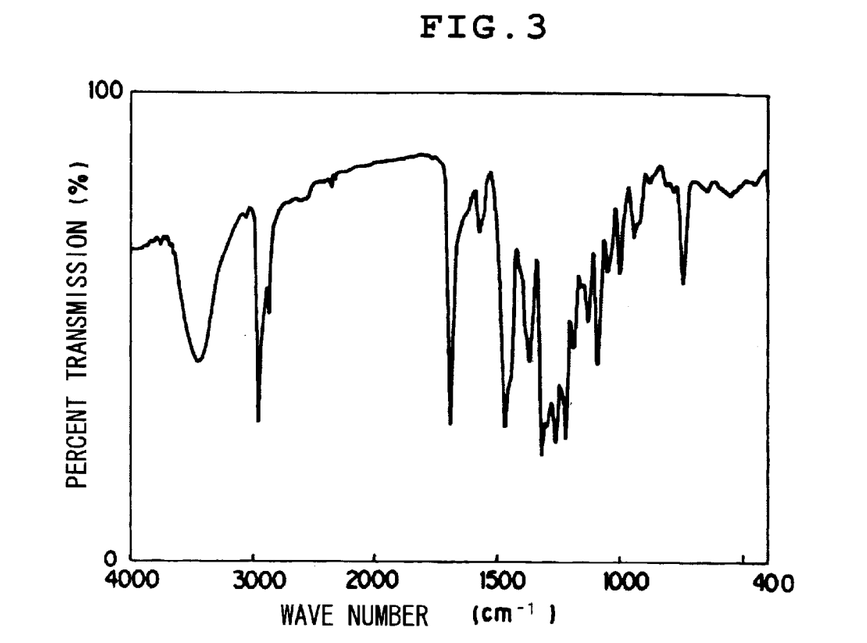
FIG. 3 is a Fourier transform infrared absorption spectrum of compound (46) in Example 2.

The FT-IR spectrum of the compound obtained is shown in FIG. 3.

Figure 4:
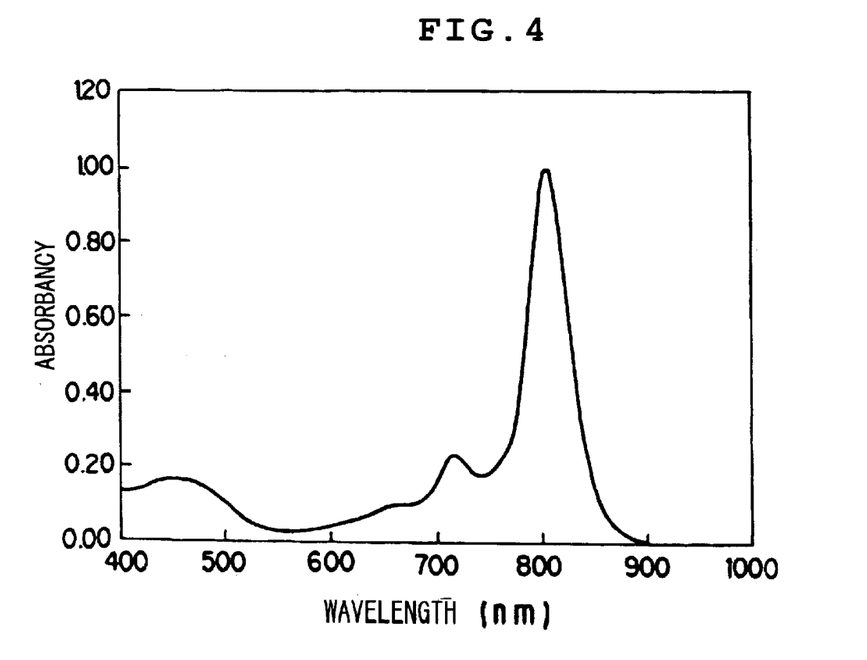
FIG. 4 is an absorption spectrum of compound (46) in Example 2 as measured in toluene.

The VIS-NIR absorption spectrum of the compound is shown in FIG. 4.

Example 3
Synthesis of Compound (50)

Except that 4.3 g of iso-valeric anhydride was used in lieu of 2.4 g of acetic anhydride, the procedure of Example 1 was repeated to give 5.4 g of compound (50) as green powders.

The elemental analysis, absorption maxima ($\lambda_{max}$) and gram-absorption coefficient ($\epsilon g$) of this compound were as follows.

Elemental analysis ($C_{116}H_{140}N_{12}O_{13}S_4V$):MW=2087.9

|  | C | H | N | V |
|---|---|---|---|---|
| Calcd. (%): | 66.67 | 6.75 | 8.04 | 2.44 |
| Found (%): | 66.70 | 6.78 | 8.02 | 2.4 |

$\lambda_{max}$: 804 nm (in toluene); $\epsilon g$: $9.71 \times 10^4$ ml/g·cm (in toluene).

Figure 5:
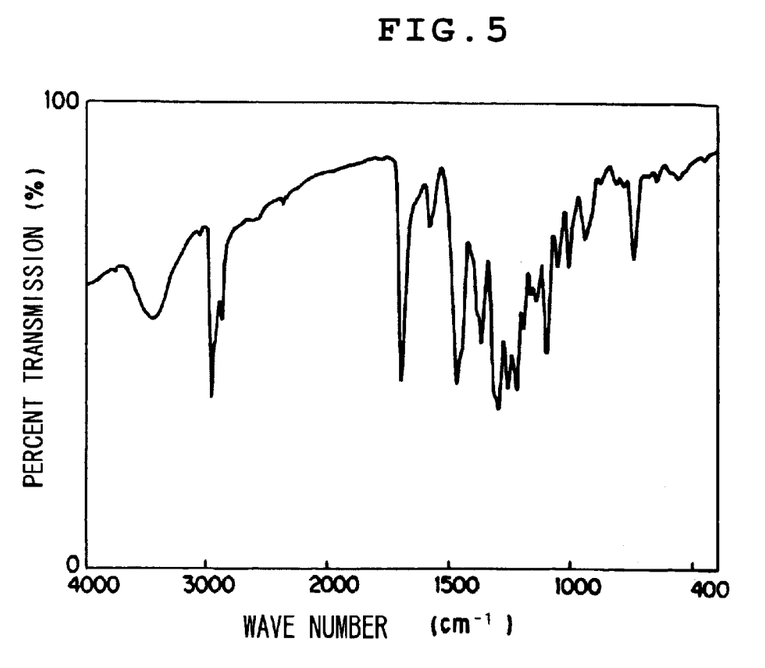
FIG. 5 is a Fourier transform infrared absorption spectrum of compound (50) in Example 3.

The FT-IR spectrum of the compound obtained is shown in FIG. 5.

Figure 6:
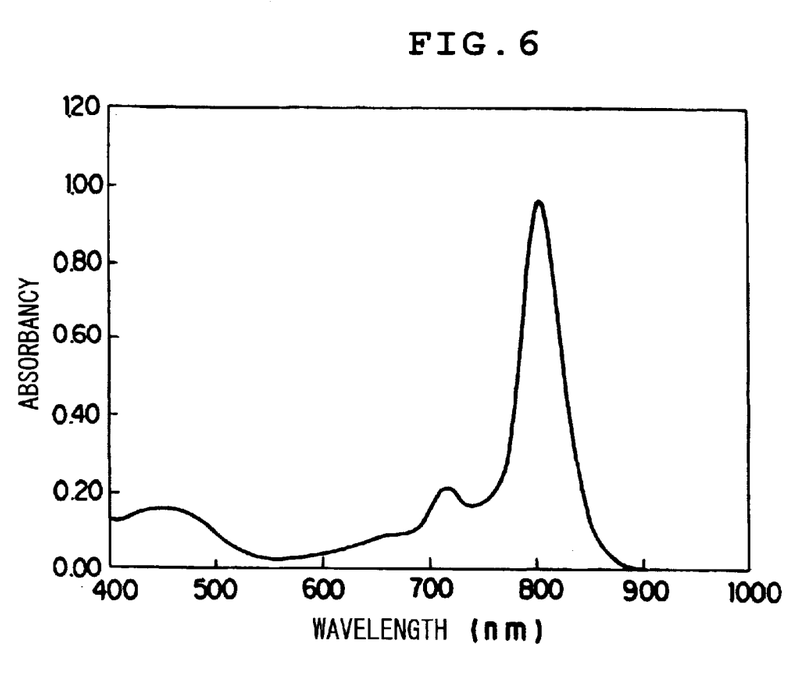
FIG. 6 is an absorption spectrum of compound (50) in Example 3 as measured in toluene.

The VIS-NIR absorption spectrum of the compound is shown in FIG. 6.

Example 4
Production of a Near-infrared Light-absorbing Material

Using a wire bar, a polyethylene terephthalate (PET) film having an average thickness of 5 μm was coated with a solution of the binder Delpet 80N (Asahi Kasei Kogyo; acrylic resin) (10 g) and compound (33) (0.2 g) in toluene-methyl ethyl ketone (1:1; 90 g) in a dry thickness of about 5 μm to prepare a test sample.

The beam of a single-mode semiconductor laser (wavelength 830 nm) was condensed with a condenser and focused to a beam diameter of 10 μm on the surface of said test sample. The semiconductor laser was set so that the laser power reaching the surface could be varied within the range of 50~200 mW and the test sample was irradiated with a single pulse with a pulse width of 20 μs. Observation of the irradiated sample under the light microscope revealed that a through-hole with a diameter of about 10 μm was formed when the laser power reaching the surface was set to 50 mW.

Example 5
Production of a Near-infrared Light-absorbing Material

Except that compound (46) (0.2 g) was used in lieu of compound (33) (0.2 g), the procedure of Example 4 was repeated. Observation of the irradiated sample revealed that a through-hole with a diameter of about 10 μm was formed when the laser power on the surface was set to 50 mW.

Example 6
Production of a Near-infrared Light-absorbing Material

Except that compound (50) (0.2 g) was used in lieu of compound (33) (0.2 g), the procedure of Example 4 was repeated. Observation of the irradiated sample revealed that a through-hole with a diameter of about 10 μm was formed when the laser power on the surface was set to 50 mW.

Example 7

Manufacture of an Original Plate for Direct Printing Plate Making (Formulation of a Subbing Layer)

A gelatin subbing layer (primer layer) was formed on a 175 μm-thick polyethylene terephthalate film in a dry thickness of 0.2 μm.

(Formation of a Photothermal Conversion Layer)

The above polyethylene terephthalate film formed with the gelatin subbing layer was coated in superimposition with a coating dope of the following formulation in a dry thickness of 2 μm to construct a photothermal conversion layer.

| | |
|---|---|
| Compound (33) | 0.1 wt. part |
| Crysbon 3006LV | 5.0 wt. parts |
| (Dainippon Ink and Chemicals; polyurethane) | |
| Solsperse S27000 (ICI) | 0.4 wt. part |
| Nitrocellulose | 4.2 wt. parts |
| (containing 30% n-propanol) | |
| Xylylenediamine (1 M)-glycidyl methacrylate (4 M) adduct | 2.0 wt. parts |
| Ethyl Michler's ketone | 0.2 wt. part |
| Tetrahydrofuran | 90 wt. parts |

(Formulation of a silicone rubber layer)

Using a coating dope of the following formulation, a silicone rubber layer was formed in a dry thickness of 2 μm on the above photothermal conversion layer.

| | |
|---|---|
| α, ω-Divinylpolydimethylsiloxane | 9.0 wt. parts |
| (degree of polymerization ca 700) | |
| $(CH_3)_3Si-O-(SiH(CH_3)-O)_8-Si(CH_3)_3$ | 0.6 wt. part |
| Polydimethylsiloxane | 0.5 wt. part |
| (degree of polymerization ca 8000) | |
| Olefin chloroplatinate | 0.08 wt. part |

| | |
|---|---|
| Inhibitor $HC\equiv C-C(CH_3)_2-O-Si(CH_3)_3$ | 0.07 wt. part |
| Isopar G (Esso Chemical) | 55 wt. parts |

Using a semiconductor laser having a beam diameter of 10 μm and an emission wavelength of 830 nm, writing was made on the original plate obtained above with the power on the plate surface being controlled at 110 mW. As a result, a printing plate of sharp edge definition was obtained with a laser recording sensitivity of 200 mJ/cm$^2$ and a resolution of 8 μm.

Example 8

Manufacture of an Original Plate for Direct Printing Plate Making

Except that compound (46) (0.1 wt. part) was used in lieu of compound (33) (0.1 wt. part), the procedure of Example 7 was repeated to produce an original plate.

Using a semiconductor laser having a beam diameter of 10 μm and an emission wavelength of 830 nm, writing was made on the original plate obtained above, with the power on the plate surface being controlled at 110 mW. As a result, a printing plate of sharp edge definition was obtained with a laser recording sensitivity of 200 mJ/cm$^2$ and a resolution of 8 μm.

Example 9

Manufacture of an Original Plate for Direct Printing Plate Making

Except that compound (50) (0.1 wt. part) was used in lieu of compound (33) (0.1 wt. part), the procedure of Example 7 was repeated to produce an original plate.

Using a semiconductor laser having a beam diameter of 10 μm and an emission wavelength of 830 nm, writing was made on the original plate obtained above, with the power on the plate surface being controlled at 110 mW. As a result, a printing plate of sharp edge definition was obtained with a laser recording sensitivity of 200 mJ/cm$^2$ and a resolution of 8 μm.

EFFECT OF THE INVENTION

The phthalocyanine compound of general formula (I) absorbs little in the visible region of the spectrum (in particular,. 500~600 nm) and is of light color by itself and readily soluble in polar solvents. The near-infrared light-absorbing material containing this compound is highly sensitive to laser light and can be used with advantage in the field of laser thermal transfer recording materials or laser thermal recording materials permitting high-speed recording and giving high-density and high-quality images and particularly in the field of near-infrared light-absorbing filters for plasma display, secret inks and so forth.

Furthermore, the phthalocyanine compound of general formula (I) has exceptionally high solubility in the various solvents used in the manufacture of original plates for direct printing plate making as well as good compatibility with various binder reins so that it can be easily formulated into coating compositions to contribute to the formation of uniform films, thus being particularly suited for the manufacture of original plates for direct printing plate making.

What is claimed is:

1. A phthalocyanine compound of the general formula (I):

(I)

wherein $R_1$, $R_2$, $R_3$, $R_4$, $R_5$, $R_6$, $R_7$ and $R_8$ each represents alkyl or alkoxyalkyl; $X_1$, $X_2$, $X_3$, $X_4$, $X_5$, $X_6$, $X_7$ and $X_8$ each represents sulfur or >$NR_9$; $X_1$=(either $X_3$ or $X_4$)=(either $X_5$ or $X_6$)=(either $X_7$ or $X_8$)=sulfur and $X_2$=(the other one of $X_3$ and $X_4$)=(the other one of $X_5$ and $X_6$)=(the other one of $X_7$ and $X_8$)=>$NR_9$; $R_9$ represents an acyl group which may optionally be substituted or an aroyl group which may optionally be substituted; M represents a couple of hydrogen atoms, a divalent metal, a trivalent metal derivative or a tetravalent metal derivative.

2. The phthalocyanine compound defined in claim 1 wherein $R_1$, $R_2$, $R_3$, $R_4$, $R_5$, $R_6$, $R_7$ and $R_8$ each is a straight-chain or branched-chain alkyl group containing 1~12 carbon atoms or an alkoxyalkyl group containing a total of 2~12 carbon atoms.

3. The phthalocyanine compound defined in claim 2 wherein $R_9$ is an optionally substituted acyl group containing a total of 2~18 carbon atoms or an optionally substituted aroyl group containing a total of 7~12 carbon atoms.

4. The phthalocyanine compound defined in claim 2 wherein M is Cu, Zn, Co, Ni, Pd, Pb, MnOH, AlCl, FeCl, InCl, $SnCl_2$, VO or TiO.

5. The phthalocyanine compound defined in claim 2 wherein M is Cu, Zn, Co, Ni, Pd, Pb, MnOH, AlCl, FeCl, InCl, $SnCl_2$, VO or TiO.

6. The phthalocyanine compound defined in claim 2 wherein $R_9$ is an optionally substituted acyl group containing a total of 2~18 carbon atoms or an optionally substituted aroyl group containing a total of 7~12 carbon atoms.

7. The phthalocyanine compound defined in claim 6 wherein M is Cu, Zn, Co, Ni, Pd, Pb, MnOH, AlCl, FeCl, InCl, $SnCl_2$, VO or TiO.

8. The phthalocyanine compound defined in claim 1 wherein M is Cu, Zn, Co, Ni, Pd, Pb, MnOH, AlCl, FeCl, InCl, $SnCl_2$, VO or TiO.

9. The phthalocyanine compound defined in claim 1 wherein $R_1$, $R_2$, $R_3$, $R_4$, $R_5$, $R_6$, $R_7$, and $R_8$ is each a straight-chain or branched-chain alkyl group containing 1–8 carbons atoms or an alkoxyalkyl group containing a total of 3–6 carbon atoms.

10. The phthalocyanine compound defined in claim 1 wherein $R_1$, $R_2$, $R_3$, $R_4$, $R_5$, $R_6$, $R_7$, and $R_8$ is an alkyl group selected from the group consisting of methyl, ethyl, n-propyl, isopropyl, n-butyl, isobutyl, sec-butyl, n-pentyl, isopentyl, neopentyl, n-hexyl, isohexyl, sec-hexyl, 2-ethylbutyl, n-heptyl, isoheptyl, sec-heptyl, n-octyl, 2-ethylhexyl and n-decyl or an alkoxyalkyl group selected from the group consisting of methoxymethyl, methoxyethyl, methoxypropyl, methoxybutyl, ethoxyethyl, ethoxypropyl, ethoxybutyl, n-propoxyethyl, iso-propoxyethyl, n-propoxypropyl, n-butoxyethyl, iso-butoxypropyl, n-butoxybutyl, n-pentyloxypentyl, and n-hexyloxyhexyl.

11. The phthalocyanine compound defined in claim 1 wherein $R_9$ is an acyl group selected from the group consisting of acetyl, propionyl, butyryl, iso-butyryl, valeryl, iso-valeryl, trimethylacetyl, hexanoyl, heptanoyl, octanoyl, 2-ethylhexanoyl, nonanoyl, decanoyl, undecanoyl, lauroyl, tridecanoyl, tetradecanoyl, palmitoyl, hexadecanoyl, heptadecanoyl, stearoyl, oleoyl, octadecanoyl, trifluoroacetyl, pentafluoropropionyl, perfluorooctanoyl, 6-chlorohexanoyl, 6-bromohexanoyl, methoxyacetyl, 3,6-dioxaheptanoyl or an aroyl group selected from the group consisting of benzoyl, o-toluoyl, m-toluoyl, p-toluoyl, o-chlorobenzoyl, m-chlorobenzoyl, p-chlorobenzoyl, o-fluorobenzoyl, m-fluorobenzoyl, p-fluorobenzoyl, o-acetylbenzoyl, m-acetylbenzoyl, p-acetylbenzoyl, o-methoxybenzoyl, m-methoxybenzoyl, p-methoxybenzoyl, pentafluorobenzoyl, p-(trifluoromethyl)benzoyl, 1-naphthoyl, and 2-naphthoyl.

12. A method of producing the phthalocyanine compound defined in any one of claims 1–4 which comprises reacting a phthalocyanine compound of the following general formula (II) with an acid anhydride of the following general formula (III) or an acid halide of the following general formula (IV), (II)

wherein $R_1$, $R_2$, $R_3$, $R_4$, $R_5$, $R_6$, $R_7$ and $R_8$ each represents alkyl or alkoxyalkyl; $Y_1$, $Y_2$, $Y_3$, $Y_4$, $Y_5$, $Y_6$, $Y_7$ and $Y_8$ each represents sulfur or >NH and $Y_1$=(either $Y_3$ or $Y_4$)=(either $Y_5$ or $Y_6$)=(either $Y_7$ or $Y_8$)=sulfur and $Y_2$=(the other one of $Y_3$ and $Y_4$)=(the other one of $Y_5$ and $Y_6$)=(the other one of $Y_7$ and $Y_8$)=>NH; M represents a couple of hydrogen atoms, a divalent metal, a trivalent metal derivative or a tetravalent metal derivative, $$(R_9)_2O \qquad (III)$$

wherein $R_9$ represents an acyl group which may optionally be substituted or an aroyl group which may optionally be substituted, $$R_9X_9 \qquad (IV)$$

wherein $R_9$ is as defined above; $X_9$ represents halogen.

13. A near-infrared light-absorbing material containing a phthalocyanine compound defined in any one of claims 1–4.

14. An original plate for direct printing plate making which comprises a support and a layer containing the phthalocyanine compound defined in any one of claims 1–4 as formed thereon.

\* \* \* \* \*